United States Patent
Todorovic

[11] Patent Number: 6,108,934
[45] Date of Patent: Aug. 29, 2000

[54] TANNING HAIR DRIER AND HAIR STEAMER AND PROCESS OF USING

[76] Inventor: Miljko Todorovic, 8501 Cherry Valley La., Alexandria, Va. 22309

[21] Appl. No.: 09/268,308

[22] Filed: Mar. 16, 1999

[51] Int. Cl.⁷ ..................................................... A45D 20/00
[52] U.S. Cl. ................................ 34/283; 34/298; 34/427; 34/90; 34/97; 34/99
[58] Field of Search ..................... 34/90, 96, 97, 34/99, 283, 298, 427; 607/94, 95, 108, 110, 109

[56] References Cited

U.S. PATENT DOCUMENTS

| | | | |
|---|---|---|---|
| 2,677,196 | 5/1954 | Mitchell | 34/99 |
| 2,747,296 | 5/1956 | Mitchell | 34/90 |
| 3,004,540 | 10/1961 | Ronzi | 34/90 |
| 3,645,007 | 2/1972 | Scott | 34/99 |
| 3,839,621 | 10/1974 | Hariu | 219/211 |
| 4,314,138 | 2/1982 | Itoh | 219/276 |
| 4,553,339 | 11/1985 | Rigo | 34/97 |
| 4,844,069 | 7/1989 | Mori . | |
| 4,972,607 | 11/1990 | Lagace | 34/90 |

Primary Examiner—Pamela A. Wilson
Attorney, Agent, or Firm—Hunton & Williams

[57] ABSTRACT

A tanning hair dryer and/or hair steamer and process is disclosed wherein a user can receive light from an ultraviolet ray source while also receiving conditioned air from a hair dryer and/or hair steamer. The invention can either be manufactured or applied to existing hair dryers and/or hair steamer hoods by retrofitting. Two embodiments of the invention are disclosed. In the first embodiment, a tanning shield is attached to a hood by two pivotally attached attaching arms. In the second embodiment, two tanning shields are attached to the hood by universal positioning means, or means that enable the tanning shields to be placed in a number of different positions with a number of different orientations.

12 Claims, 3 Drawing Sheets

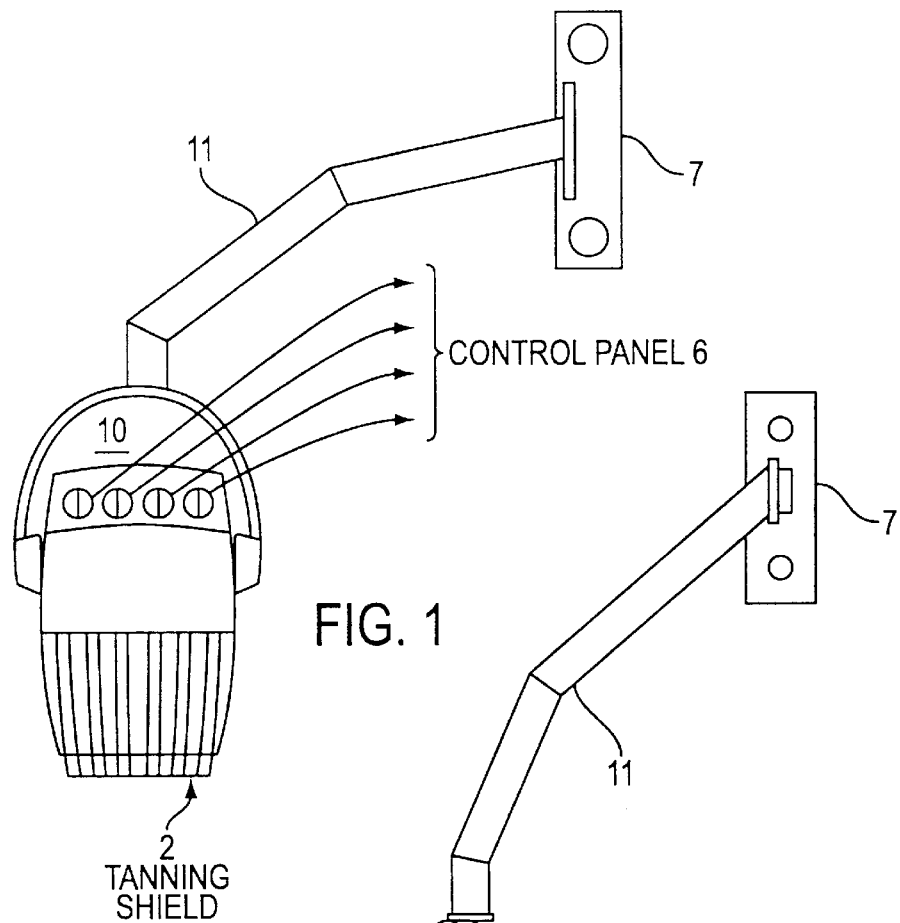
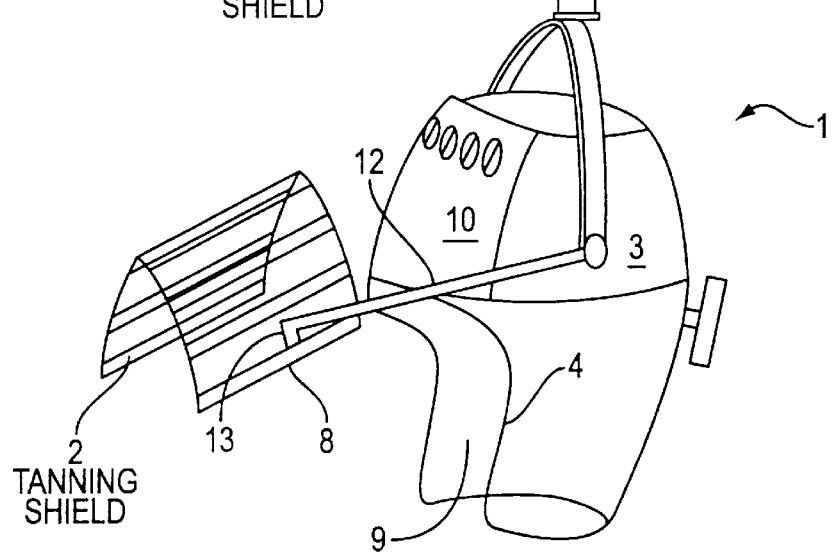

TANNING HAIR DRIER AND HAIR STEAMER AND PROCESS OF USING

FIELD OF THE INVENTION

This invention relates to a system for combined tanning, hair drying and hair steaming.

BACKGROUND OF THE INVENTION

It is known in the art that exposure of a person's skin to a form of high energy light, generally ultraviolet light, will induce an artificial tan in the person's skin. The degree of tanning is a combination of factors, including intensity of the light, duration of the exposure to the light, and the tanning individual's skin characteristics. Tanning, a term used hereinafter to designate the process of acquiring a sun tan artificially, is generally accomplished in a tanning bed.

It is also known in the art that exposure of a person's hair to heated, flowing air will increase the speed with which a person's hair can dry. Additionally, it is known that some of the apparatuses that serve to dry a person's hair have also been modified to humidify the hot air, thereby modifying the hair drying apparatus to a hair drying and steaming apparatus.

A problem that is often encountered by the prior art devices is that the time taken to steam and/or dry one's hair plus the time to tan can be longer than some individuals are willing to spend on improving their personal appearance.

Another problem is that salon or beauty parlor proprietors must purchase, and provide space for two or more separate pieces of equipment, thereby incurring greater costs. Other drawbacks also exist.

SUMMARY OF THE INVENTION

One object of the present invention is to overcome these and other drawbacks of existing devices. In accordance with the above objects, a hair dryer and steamer apparatus is used in conjunction with a tanning apparatus for the purpose of tanning an individual's face and neck while at the same time drying and/or steaming an individual's hair. In one preferred embodiment, the tanning system may be an integral component of a hair dryer/steamer. In one preferred embodiment, the tanning shield may be pivotally attached to a hair dryer/steamer hood ("hood"), allowing the operator to position the tanning shield in front of the tanning individual's face after the tanning individual's head is placed within the hood. In another embodiment, the two tanning shields may preferably be attached to a pair of arms that are pivotally attached to the hair dryer, thereby allowing the shields to be independently positioned in front of the user's face.

BRIEF DESCRIPTION OF THE DRAWINGS

FIG. 1 shows a front view of a preferred embodiment in the operational position.

FIG. 2 shows an oblique view of a preferred embodiment in the standby position.

DETAILED DESCRIPTION OF A PREFERRED EMBODIMENTS

Figure 3:
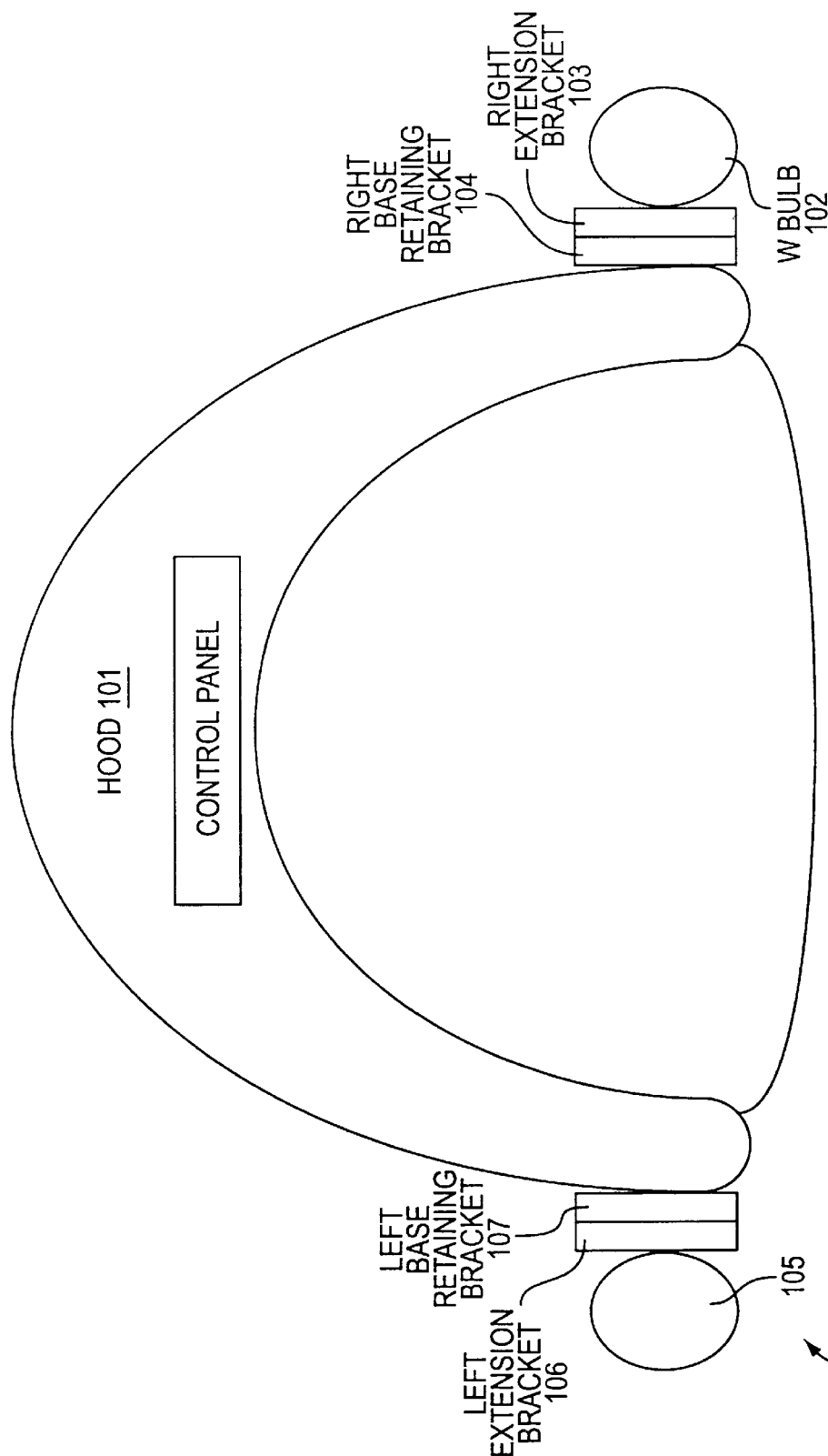
FIG. 3 shows a front view of another embodiment in the standby position.

Referring now to the drawings, it is understood that like numbers represent the same object in different figures. FIG. 1 depicts a frontal view of a preferred embodiment in the operational position. The tanning hair dryer/steamer is generally referred to by the reference number 1. The tanning hair dryer/steamer 1 is shown in the operational position, or the position in which the tanning shield 2 will be when a person's head is within the head space 9 (shown in FIG. 2).

From this front position portrayed in FIG. 1, various other features of a preferred embodiment are also visible, including the tanning shield 2, control panel 6, hood 10, mounting bracket 7, and hood-to-wall arm 11. In a preferred embodiment, the tanning hair dryer/steamer 1 is attached to a wall with the mounting bracket 7. Extending from the mounting bracket 7 is the hood-to-wall arm 11. The hood-to-wall arm 11 is depicted as three rigid members pivotally attached to one another to allow an operator to position the hood in a number of different positions. However, other configurations are possible. The invention may be practiced with any type of hair drier/steamer system that has a hood.

The control panel 6 is represented by four proximally located control knobs on a single surface of the hood. In a preferred embodiment, these knobs comprise a timing knob for the dryer/steamer function of the tanning hair dryer/steamer 1, a timing knob for the tanning function of the tanning hair dryer/steamer 1, and a temperature control and fan control for the air in the tanning hair dryer/steamer 1. Various combinations of these controls as well as additional control features could be added to the control panel. Additionally, the control panel could be positioned so that all or some of the functions could be controlled by the person utilizing the tanning hair dryer/steamer 1, thereby eliminating or reducing the need for an equipment operator. Additional controls could be added, including various music or noise controls, communication controls, or any other controls desired by the user or operator.

FIG. 2 depicts an oblique view of the tanning hair dryer/steamer 1 wherein the face shield is in the standby mode. The standby mode of a preferred embodiment enables a user to place his or her head within the head space 9 with relative ease.

The tanning shield 2 may be attached to the hood 10 by the attachment arm 12 (a right side attachment arm is not shown). The attachment arm 12 may be pivotally affixed to the hood 10 and the tanning shield 2 at pivot points 3 and 13 respectively. Pivot points 3 and 13 preferably utilize any suitable pivotal type attachment. Pivot point 3 may additionally serve to pivotally attach the hood 10 to the hood-to-wall arm 11. Attachment arm 12 may be a single, rigid member in a preferred embodiment for the purpose of decreased cost of manufacture. However, it is possible to construct the attachment arm with a plurality of pivotally attached rigid members, or a malleable, semi-rigid member in order to enable the tanning shield 2 to be placed at the position desired by the operator or user.

The tanning shield 2 preferably has a number of bulbs which emit ultraviolet light when activated. Although the bulbs are represented as being vertically aligned in relation to the tanning shield 2 when in operational mode, it is possible to utilize tanning bulbs in any pattern and remain within the scope of the current invention.

An ideal distance from the face to the tanning shield 2 will depend partially upon the distance between the bulbs utilized in the tanning shield 2: the smaller the distance between each of the bulbs, the smaller the ideal distance becomes. In a preferred embodiment, there are at least five bulbs, and the distance from the tanning shield 2 to the individual's face preferably ranges from about four to about six inches, depending upon the features of the individual who is using the tanning hair dryer/steamer 1. As stated previously, it is possible to modify the attachment arm 12 in order to allow greater flexibility in placing the tanning shield 2 to provide a more controlled tanning process.

Figure 4:
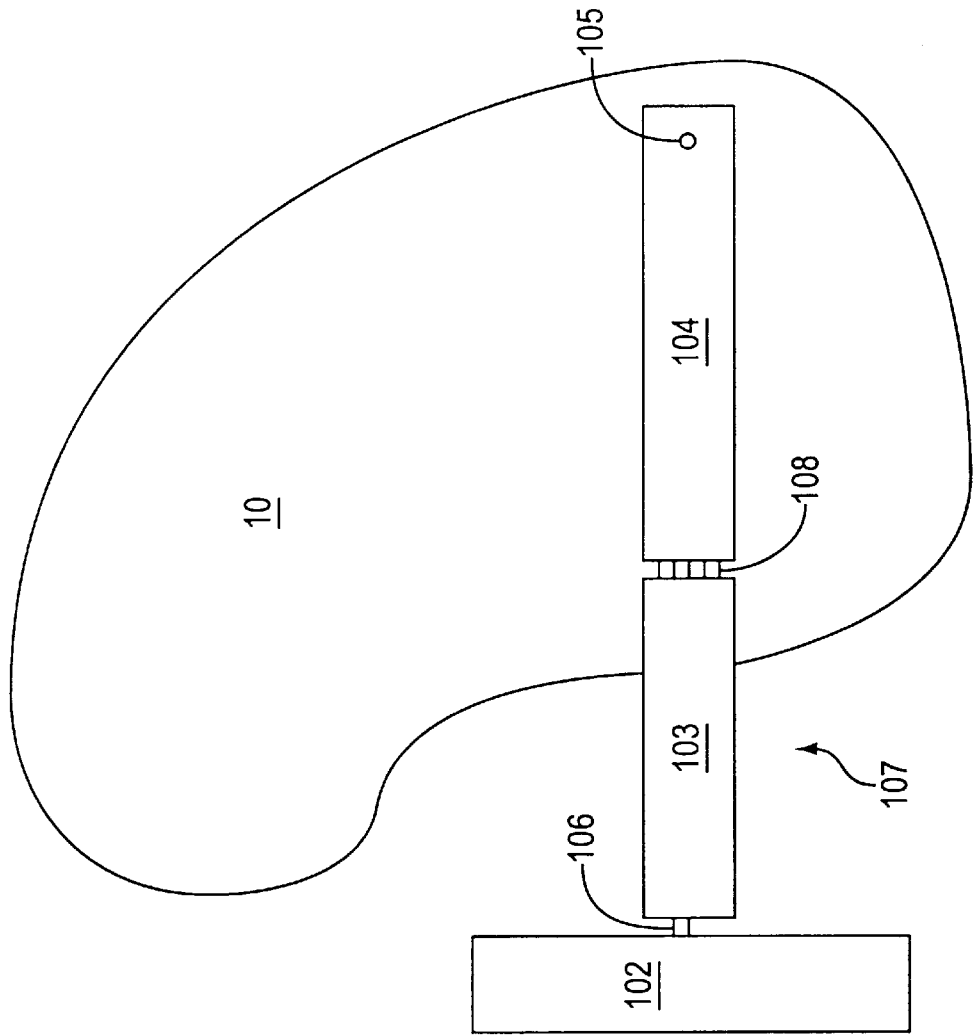
FIG. 4 shows a side view of another embodiment in the operational position.

FIG. 3 depicts another view of the second embodiment in standby position. FIG. 4 represents a side view of the second embodiment in the operational position. FIG. 4 portrays a universal attaching mechanism of another embodiment, and identifies each of the individual elements. As seen in FIG. 4, the attaching mechanism 107 has two brackets 103 and 104. A first bracket 104 may be attached to the hood 10 by a suitable attachment. For example, a ball-and-socket attachment 105 could be used, thereby giving the first bracket 104 freedom to move about the fixed point of the ball-and-socket type attachment 105. Other attachment mechanisms are possible.

First bracket 104 preferably allows for movement of the hinge 108 away from the hood 10. The second bracket 103 may be attached to the first bracket 104 by a hinge 108. The hinge 108 is preferably capable of opening beyond greater than 180 degrees, its degree of opening being limited by contact with the hood 10 or first bracket 104. The tanning shield 102, which in one embodiment is a singular ultraviolet bulb and ultraviolet bulb case, is attached to the second bracket 103 by another ball-and-socket type attachment 106. Electrical connections (not shown) could either be run through the brackets and to the tanning shields or they could be attached to the outside of the attaching mechanism for the purpose of providing power to the tanning shields.

Although this embodiment discloses a tanning shield comprising a single ultraviolet bulb and ultraviolet bulb case, the present invention could be applied with any type of tanning shield. For example, the tanning shield could comprise a number of horizontally or vertically aligned lights, a matrix of lights, or any other type of light arrangement that is known in the art.

The current invention could be used either as a manufactured system or a retrofit. In the event that the current invention serves as a retrofit, or modification after manufacture to a hair dryer and/or hair steamer, the attaching arms 107 also serve as a retrofitting means. Specifically, a retrofit assembly can be adapted to a hood either in the manner of the first or second disclosed embodiment, or in any other method that will allow a face shield to be movably attached to the hood. For example, an attachment could be drilled or glued to the hood to serve as the ball of the ball-and-socket type attachment of the second embodiment.

The disclosed embodiments provide tanning only to an individuals face and neck, but it is within the scope of the invention to utilize a system that provides tanning to the whole body while drying and/or steaming the hair. It is also within the scope of the present invention to include lights within the hood of the present invention.

What is claimed is:

1. An apparatus for tanning skin, drying hair and steaming hair comprising:

a hood, comprising a hair dryer and a hair steamer;

at least two attaching arms, each of the two attaching arms having first ends and second ends, wherein each of the first ends pivotally attach to the hood;

a tanning shield that attaches to each of the second ends of the two attaching arms; and at least one tanning bulb, connected to the tanning shield, that emits radiation comprising at least ultraviolet light.

2. The apparatus of claim 1 further comprising:

pivotal attachments between the tanning shield and each of the second ends of the attaching arms.

3. The apparatus of claim 2 further comprising:

a control panel, mounted on the hood, comprising at least two controls.

4. The apparatus of claim 1, wherein:

each of the two attaching arms are malleable, semi-rigid apparatuses.

5. The apparatus of claim 1, wherein:

the hood further comprises attachment means that enables each of the first ends to be attached to the hood.

6. An apparatus for tanning hair drying and hair steaming comprising:

a hood, comprising a hair dryer and a hair steamer;

at least two attaching arms, each of the attaching arms attached to hood;

at least one tanning shield attached to each of the at least two attaching arms; and at least one tanning bulb, connected to the at least one tanning shield, for emiiting radiation capable of tanning skin.

7. The apparatus of claim 6, wherein:

each of the at least two attaching arms further comprise at least two brackets;

a first of the at least two brackets pivotally attaches to the hood; and the at least one tanning shield pivotally attaches to another of the at least two brackets.

8. The apparatus of claim 6, wherein:

each of the at least two attaching arms is a universal positioning means.

9. The apparatus of claim 6, wherein:

the hood further comprises attachment means that enables the at least two attaching arms to be attached to the hood.

10. A process for enabling a hair drying and steaming apparatus to tan a user's skin, the process comprising the steps of:

providing a hair drying and steaming apparatus comprising a drying and steaming hood;

providing a tanning shield that attaches to the drying and steaming hood; and providing at least one tanning bulb that emits radiation capable of tanning the user's skin.

11. The process of claim 10, further comprising the step of:

providing a control panel comprising at least one control means that enables the user to select various control parameters.

12. The process of claim 10, further comprising the step of:

providing a control panel comprising at least one control means that enables an operator other than the user to select various control parameters.

* * * * *